(12) United States Patent
Falus

(10) Patent No.: US 8,680,240 B1
(45) Date of Patent: *Mar. 25, 2014

(54) TISSUE SEALANT FOR USE IN NON-COMPRESSIBLE HEMORRHAGE

(71) Applicant: George David Falus, New York City, NY (US)

(72) Inventor: George David Falus, New York City, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/666,545

(22) Filed: Nov. 1, 2012

(51) Int. Cl.
*A61K 35/14* (2006.01)

(52) U.S. Cl.
USPC .......................................... 530/381; 514/13.7

(58) Field of Classification Search
None
See application file for complete search history.

(56) References Cited

U.S. PATENT DOCUMENTS

| 5,489,437 | A * | 2/1996 | Marra | 424/443 |
| 8,314,211 | B2 * | 11/2012 | Falus | 530/381 |
| 2011/0066182 | A1 * | 3/2011 | Falus | 606/214 |

OTHER PUBLICATIONS

Sheehan, John C. and Nafissi-V, M. Mehdi; "alpha lactams. VI. Photochemistry of alpha lactams." J. Am. Chem. Soc. (1969) 91(5) p. 1176-1178.*
Dill, Ken A and Shortle, David; "Denatured states of proteins." Annu. Rev. Biochem. (1991) 60 p. 795-825.*
Ivancev-Tumbas, Ivana et al; "THe effect of different drinking water treatment processes on the rate of chloroform formation in the reactions of natural organic matter with hypochlorite." Wat. Res. (1999) 33(18) p. 3715-3722.*
Chauvin, Remi; ""Carbomers". I. A general concept of expanded molecules." Tet. Let. (1995) 36(3) p. 397-400.*
Latallo, Zbigniew S et al; "Influence of pH, ionic strength, neutral ions, and thrombin on fibrin polymerization." Am. J. Physiol. (1962) 202(4) p. 675-680.*
Mackensen, Andreas et al; "Presence of IgE antibodies to bovine serum albumin in a patient developing anaphylaxis after vaccination with human peptide-pulsed dendritic cells." Cancer Immunol. Immunother. (2000) 49(3) p. 152-156.*
Van Slyke, Donald D. and Cullen, Glenn E.; "Studies of acidosis. I. The bicarbonate concentration of the blood plasma; its significance and its determination as a measure of acidosis." J. Biol. Chem. (1917) 30 p. 289-346.*
GenBank entry for human albumin, accession No. AAA98797, entered 1996.*
GenBank entry for bovie albumin, accession No. AAA51411, entered 2002.*
Wasserman, Moises et al; "Increase of a calcuim independent transglutaminase activity in the euythrocyte during the infection with plasmodium falciparum." Mem. Inst. Oswaldo. Cruz (1999) 94(1) 95-100.*

* cited by examiner

Primary Examiner — Cecilia J Tsang
Assistant Examiner — Fred Reynolds

(57) ABSTRACT

ClotFoam is a sealant and hemostatic agent for use in cases of non-compressible hemorrhage for moderate to severe bleeding. It can be applied in the operating room through laparoscopic ports, or directly over lacerated tissue in laparotomy procedures or outside the operating room through a mixing needle and/or a spray injection method following intracavitary severe trauma or surgery. Its crosslinking technology generates an adhesive scaffold that carries a fibrin sealant required for hemostasis. Clotfoam produces a foam that spreads throughout a body cavity reaching the lacerated tissue to seal tissue and promote the coagulation cascade. The composition is biocompatible and non-inflammatory.

The invention uses fibrin monomer polymerized by a change of pH as active sealing component. The viscoelastic properties of the foam as well as the rapid formation of a fibrin clot ensure that the sealant remains at the site of application without being washed away by blood.

21 Claims, 9 Drawing Sheets

Application Device

Mode of Action

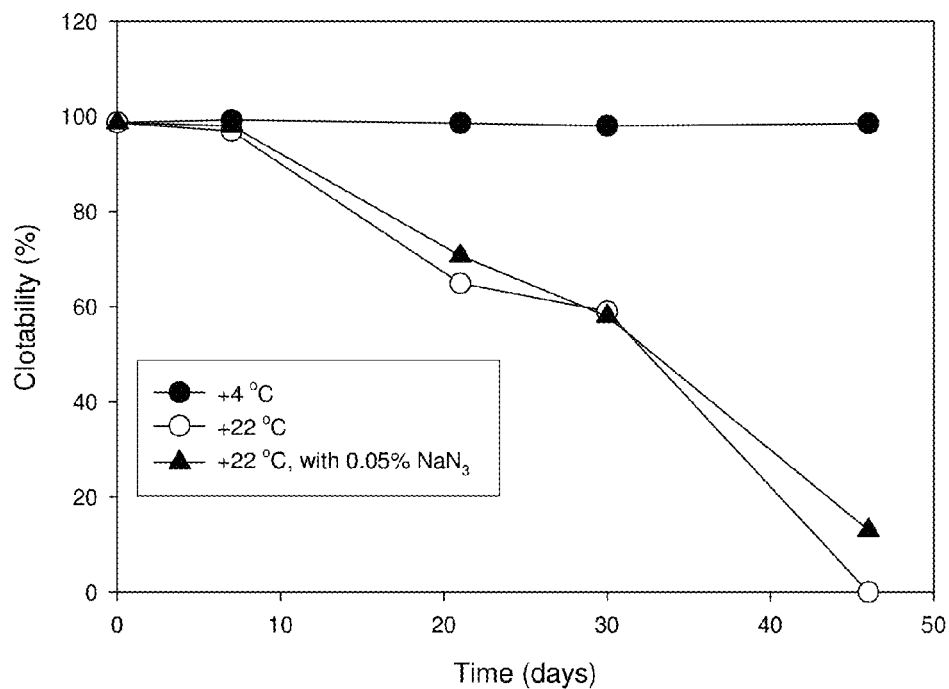
Figure 8
Biocompatibility of Human Fibroblasts exposed to ClotFoam
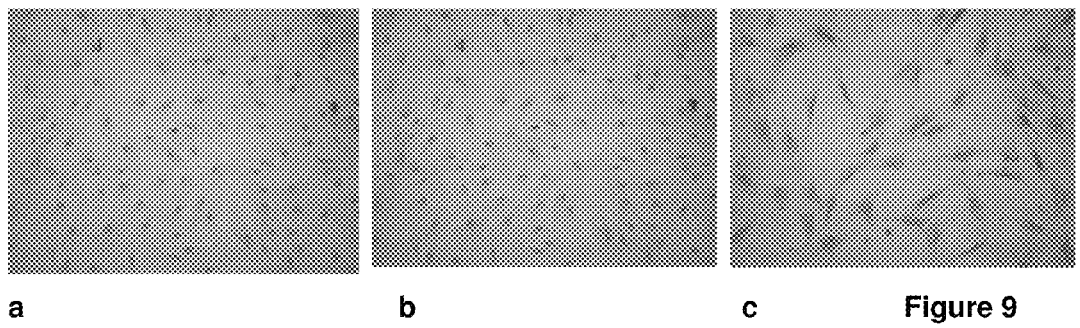
a  b  c  Figure 9

Laparoscopy Surgery of Liver Wound Grade IV treated with ClotFoam

Median Blood Pressure of Swine subjected to Liver Wound grade IV Treated with ClotFoam Median Blood Pressure of Swine subjected to Liver Wound grade IV non-treated

TISSUE SEALANT FOR USE IN NON-COMPRESSIBLE HEMORRHAGE

FIELD OF THE INVENTION

The present invention, which has been trademarked as ClotFoam®, is generally related to an adhesive sealant composition and hemostatic agent; which may be used to bond or seal tissue in vivo without compression, stitches or staples. Its adhesive and sealing capacity is the result of viscoelastic properties—such as gel strength—and the clotting properties of the incorporated fibrin component. It is particularly related to a four component solutions; which are mixed together as it is applied to tissue, and then cured in vivo in order to bond tissue, in order to seal tissue to prevent or control intracavitary or internal hemorrhage. This is a modification to the composition disclosed in U.S. Pat. No. 8,313,211.

BACKGROUND OF THE INVENTION

Traumatic injury is a frequent cause of morbidity and mortality worldwide. Over 40% of the trauma cases admitted at hospitals in the USA is due to road traffic accidents. Hemorrhage is the primary cause of death on the battlefield in conventional warfare (1). The vast majority of these deaths occur in the field before the injured can be transported to a treatment facility (2). Almost 50% of combat fatalities in Iraq and Afghanistan, and up to 80% of civilian trauma fatalities within the US, are attributed to uncontrolled hemorrhage (3).

The major causes of death in this group are hemorrhage (50%) and neurological trauma (36%); whereas, the rest are from devastating multiple injuries. Even when the injured survive long enough to be transported to a medical facility, hemorrhage still remains the leading cause of late death and complications (2). Abdominal injuries pose a formidable problem, especially in young adults (4-8). Being the largest solid organs within the abdomen, the liver and the spleen are the most frequently injured organs (9-10).

Massive bleeding from the liver is currently controlled by Pringle's maneuver or packing of the wound, both of which procedures require surgical intervention, and cannot be applied in the battlefield or at the site of accident (11, 12). Spleen trauma can bleed profusely with minimal injury (10-12). Early and effective hemorrhage control can save more lives than any other measure. But since all current haemostatic agents for intracavitary bleeding are designed to be used in the operating room with the cavity wide open (13), not in an emergency at the site of accident or in the battlefield hemorrhage is often fatal. Also, certain types of surgery such as laparoscopic procedures or brain surgery—as well internal bleeding that today requires compression—could be treated in a less invasive manner.

Current solutions and limitations. Biological glues which can adhere to tissues are known. In general, the synthetic adhesives are used for the tight sealing of vessels or of lungs and for "gluing" the edges of skin incisions. These glues are eliminated, in general after the cicatrization of the wound—by biodegradation, absorption or by simple detachment in the form of scabs. Various technologies have been developed for the formulation of tissue adhesives. Some of them are of synthetic origin, such as the glues based on cyanoacrylates (2-butyl cyanoacrylate, 2-octyl cyanoacrylate), or on synthetic polymers; and others contain biological materials such as collagen or fibrin which, in addition, have hemostatic properties and also act by controlling bleeding. As a result of their hemostatic and adhesive properties, sealants, and particularly fibrin sealants—have been extensively used in most surgical specialties for over two decades to reduce blood loss and post-operative bleeding because of the ability to adhere to human tissue as it polymerizes (14, 15, 16). These compounds are used to seal or reinforce wounds that have been sutured or stapled; they can also be used with pressure over an injured area. Fibrin sealants are biological adhesives that mimic the final step of the coagulation cascade. (13)

There are several commercial products available (Floseal, Gelfoam, Evicel, Floseal)(16-18). However, these products have significant limitations which have prevented their widespread use in emergency medicine (trauma) and laparoscopic surgery. All existing haemostatic agents for intracavitary bleeding are designed to be used in the operating room and not in an emergency—e.g., at the site of accident or in the battlefield; and all require compression. One of the major limitations encountered in the development and/or use of tissue adhesive and sealant compositions for non-compressible hemorrhage is their inability to form a sufficiently strong bond to tissues and to develop a method of application. Therefore, tissue adhesives and sealants have to be employed in combination with compression methods, sutures and/or staples so as to reduce the tissue-bonding strength required for acceptable performance. However, there are many situations where the use of sutures and/or staples is undesirable, inappropriate or impossible. The difficulty of the adhesive matrix in forming a strong interface or bonding with tissues is most likely due to several factors: The intracavitary free blood or flowing blood does not allow the compounds that promote coagulation to reach the bleeding source; and various proteins in the tissue are not readily amenable to non-covalent and/or covalent interactions with the tissue adhesive or sealant components as applied and/or during and after curing. As a result, for most tissues and adhesive and sealant systems; failures are generally believed to occur at the interface between the cross-linked adhesive matrix and one or more tissue-associated proteins—such as collagen, actin and myosin (19,20). Another important limitation is the fact that glues are carried by supports that are left inside the body until biodegraded, and cannot be washed or eliminated immediately after surgery. A third important limitation is the inflammatory reaction leading to adverse events created by some of the compounds included in the formulation.

The Present Alternative Approach:

Clotfoam is an agent that can achieve hemostasis without compression and/or sutures that are required to stop bleeding from severe intracavitary trauma outside the operating room, without triggering significant inflammatory reaction. Non-compressible technologies are also useful in the operating room where compression cannot be applied (e.g. laparoscopic surgery, neurosurgery, etc.), In order to resist the flow of blood, the adhesive matrix must form a strong interface in a matter of seconds, and bond with tissues in the midst of flowing blood; remaining at the lacerated site to form a clot.

The ability of the present agent to adhere to human tissue is related to the internal structure of the scaffold carrying the fibrin sealant that translates into the necessary viscoelastic and adhesive properties produced by the gelling components as it polymerizes. Rapid formation of the hydrogel, and a minimum polymerization time to produce an adhesive gel that contains the necessary components to develop a functional fibrin clot over lacerated bleeding tissue, is are clinically important. Instant tissue sealant adhesion is desirable to ensure that the sealant functions on contact and remains at the site of application without being washed away by blood or displaced by movement of the target tissue. (21)

In our approach, these functions are met through a) the in-situ generation of a three-dimensional polymeric crosslinking chemistries network that is bonded to the tissue by non-covalent bonds, and b) the viscoelastic characteristics of foam enhanced by a gelling component, producing a very sticky matrix that attaches to lacerated tissue and wet surfaces without triggering a severe inflammatory reaction that cannot resolve within 15 days; and c) the instant formation of a strong fibrin clot stabilized by Calcium independent transglutaminase enzyme ACTIVA®. Stickiness and other viscoelastic properties contribute substantially to the ability of the fibrin polymer to form a blood clot amid severe bleeding and achieve hermostasis.

Composition.

ClotFoam incorporates fibrin monomer in solution, ready to polymerize at change of pH produced by the dialysis method as described in U.S. Pat. No. 8,367,802 Falus, et al. "A Method to Produce Fibrin Monomer in Acid Media for Use as Tissue Sealant." Date: Jun. 18, 2009. (Falus, et al), which is embedded in a hydrogel scaffold. The scaffold is cross-linked in the presence of calcium independant transglutaminase enzyme (ACTIVA) while the fibrin polymer is cross-linked by both active and by activated Factor XIII presence in the blood, forming α-α and γ-γ dimmers. Both polymers, fibrin and scaffold, when mixed through an application device (FIG. 1), and cross-linked in situ, fulfill three objectives or functions: a) allow non-invasive application and dissemination of the agent in the peritoneal or other body cavities; b) adhere and compress lacerated or wound tissue to prevent flow of blood; and c) maintain the necessary components over the wound, to produce a fibrin clot and stimulate the coagulatory coagulation cascade.

The scaffold uses gelatin as the "structural" protein cross-linked with polyacrylic acid, cross-linked with allyl ethers of sucrose (Carbomer homopolymer) containing not less than 56.0 percent and not more than 68.0 percent of carboxylic acid; with a viscosity of a neutralized 0.5 percent aqueous dispersion between 30,500 and 39,400 centipoises, and ACTIVA®, a calcium independent transglutaminase enzyme, in the presence of a non-inflammatory gel strengthener or enhancer selected from the group consisting of alpha-galactosidase degraded carrageenan, alginate sulfate, hyaluronic salt, or hyaluronic acid; to achieve a specific viscoelastic profile that is ideal for carrying the fibrin monomer and for neutralizing its pH in order to polymerize it. (21, 22)

When polymerized by the mixing of the parts (FIG. 2 and FIG. 4), fibrin provides a critical provisional matrix at the sites of injury (23).

While the desired viscosity or gel strength can be achieved by many "gums", such as xanthan gum or similar; the charges in the molecular structure and the pro-inflammatory effect of these gums limit the choice of a non-inflammatory gel strengthener to a carrageenan depleted of its inflammatory properties by a treatment with α-galatosidase enzyme, alginates salts or hyaluronic salts. All other viscosity agents have proved to be infective ineffective in helping achieve the viscoelastic properties that produce hemostasis.

The non-invasive application and dissemination is based on the production of foam upon mixing the components; which—once injected—spreads throughout the cavity, reaching the lacerated tissue to form a fibrin clot. Other important differences with existing gels are that the proposed adhesive uses as a cross-linked structural protein, Teleostean fish gel, gelatin Type A, human serum albumin (HSA, protein), Carbomer 934 (polyacrylic acid crosslinked with perallyl sucrose), a calcium-independent crosslinking catalyst (ACTIVA); and alternative materials—such as polysaccharides and polyvinylpyrolidone, and $MgCl_2$—in addition to 'modified' Carrageenan (sulfonated polysaccharide) sucrose or alginates; or hyaluronic salts or hyaluronic acids, providing better and "intelligent" cross-linking chemistries that modify the liquid-gel state and viscosity as needed.

The ability of the matrix to achieve hemostasis depends not only the formation of fibrin itself, but also on interactions between specific-binding sites on fibrin, pro-enzymes, clotting factors, enzyme inhibitors, cell receptors and, equally importantly, the dynamics of distribution and viscoelastic attachment properties of the foam (24,25). The activity of these factors can be enhanced or improved to produce a strong clot able to stop the parenchyma bleeding in the spleen, liver and other solid organs in the abdominal cavity, cranial cavity, and soft tissue. Each part is formulated to maximize the strength of the support of fibrin clot component measured by its rheometry properties (g' and g"). Gelling time or almost instant gelation of the scaffold, gel strength measured by the stored energy of the supporting polymer (g'), ability to maintain contact adhesion in wet surfaces and rapid polymerization of the fibrin monomer and stabilization (formation of covalent bonds in the presence of ACTIVA); are central to agent's ability to deposit a clot over the wound while ensuring that the sealant remains at the site of application without being washed away by blood or displaced by movement of the target tissue (19). High tensile strength and adhesive strength (FIG. 4 3) are mechanical properties characterizing the gelatin-fibrin polymeric network produced by the agent, which are necessary for successful sealing (29). Under coagulant conditions, ACTIVA, as well as Ca ($2^+$), Mg++ and Zn++, contribute to this process by stabilizing the fibrin clot through covalent bonds. (24)

Key Attributes.

Polymerization/Adhesion. The gel foam is formed as a result of the covalent cross-linking of the gelatin chains, serum albumin and carbomer 934 in the presence of sucrose, metallic ions, and calcium independent transglutaminase enzyme.

The gel carries and supports the polymerization of fibrin monomer in solution, which is stabilized by Ca++ and ACTIVA into a fibrin clot within 1 minute of application. The gelling properties are preferably strengthened by non-inflammatory viscosity agents, selected from the group comprising alpha galactoside-treated carrageenan, or alginates or hyaluronic salts or hyaluronic acids. The clot is mechanically stable, well integrated into the scaffold, [25] and more resistant to lysis by plasmin, as compared to an uncross-linked clot [26] or to other fibrin sealants. Components of the scaffold, together with ACTIVA, facilitate the transglutaminase-mediated oligomerization of the aC-domains of fibrin-promoting integrin clustering and thereby increasing cell adhesion and spreading, which stimulates fibrin to bind avb3-, avb5- and a5b1-integrins on EC (27). The oligomerization also promotes integrin-dependent cell signaling via focal adhesion kinase (FAK) and extracellular signal-regulated kinase (ERK), which results in an increased cell adhesion and cell migration over time—powered by the effects of fish gelatin on fibroblast differentiation [28]. The presence of additional Ca+ and Zinc enhance the progression between the inflammatory response and the coagulation cascade (first stage).

The adhesion characteristics to vital human tissue and the kinetics of polymerization of the proposed agent have been tested in vitro and in vivo (FIG. 4). The data obtained provides ample evidence of the ability of Clot Foam to stop bleeding and achieve hemostasis with no compression in induced intraperitoneal non-compressible severe traumatic intracavitary damage in the swine models, including simulated damage caused by explosive devices such as those observed by the U.S. Army in Operation Iraqi Freedom and more recently in Afghanistan. The gel process begins within 6 seconds of mixing the liquid solutions, reaching gel strength of 7,000 dyn/cm2±1,000 dyn/cm2 in 10 seconds (FIG. 5) Gel state remains stable between 10 to 20 minutes. Studies of tensile static and dynamic loading of the adhesive hydrogels in bulk form demonstrated that the Young's modulus ranged from 45 to 120 kPa and that these bulk properties were higher than to those reported for hydrogels obtained from fibrin-based sealants (28). Even after being washed away, strands of ClotFoam remained attached to both of the opposing lacerated tissues.

Protein gelation. Another important component that ensures the binding of the three-dimensional polymeric network to the tissue surrounding the wound is the structural protein. ClotFoam contains Teleostean Gelatin type A in liquid phase. The raw material for the production of this gelatin is the skin from deep water fish such as cod, haddock and Pollock pollock. It is a protein derived by a mild partial hydrolysis from collagen at low temperature.

The uniqueness of fish gelatin lies in the amino acid content of the gelatin. Although all gelatins are composed of the same 20 amino acids, there can be a variation in the amount of aminoacids, proline and hydroxyproline. With lower amounts of these amino acids, there is less hydrogen bonding of gelatin in water solutions, and hence a reduction in the gelling temperature. Gelatin from cod skin gels at 10° C. (30).

Biomacromolecules like gelatin have emerged as highly versatile biomimetic coatings for applications in tissue engineering (31). The steady-state adhesion energy of 3T3 fibroblasts on gelatin film is three times higher than that on chitosan film. The better attachment of 3T3 fibroblast to gelatin is caused by the presence of adhesive domains on gelatin. Thus, bioabsorbable gelatin and polysaccharides can be used to prepare a safer and stronger hemostatic gel (32).

The sealing effect of rapidly curable 3D network of gelatin-Fibrin BSA HAS hydrogel glue on lacerated tissue has been studied in our laboratory. Upon mixing of the polymer components in aqueous solution, Schiff base is formed between the amino groups in the modified gelatin and the aldehyde groups in the modified polysaccharides, which results in intermolecular cross-linking and gel formation. Its bonding strength to it is about 225 gm cm $(-2)^{(-2)}$ when 20 wt % of an amino-gelatin (55% amino) and 10 wt % of aldehyde-HES (>84% dialdehyde) aqueous solutions were mixed. Hydrogel glue resulted in superior sealing effect.

Gelatin is widely used in medical applications. Together with water, it forms a semisolid colloidal gel. It already has been used in several life supporting applications such as plasma expanders and blood substitutes. (31) Gelatin has been suggested as a low side-effect molecule in the hemostatic variables when utilized intravenously as a volume-blood substitute in hemorrhagic shock (33). This molecule has been related to be an excellent natural attachment site for cells, as well as a material with a high degree of biocompatibility; and it is readily available to incorporate agents to it that are related to the wound healing process and coagulation.

Viscoelastic properties. Viscosity and elastic moduli at the gel point vary at differing gelatin, gel enhacers, carbomer and ACTIVA concentrations. These parameters provide a measure of the flow properties and gel strength at a single time— the gel-point; and also provide an indication of optimal distribution of the foam in the cavity—and ability to spread throughout the cavity, stick to the lacerated tissue and form a fibrin clot. The optimal concentration of components as described below, and the incorporation of a non-inflammatory gel strengthener, allow the adhesive to flow into and mechanically "interlock"—or stick—to the tissue in order to seal the wound. The gel strengthener plays a critical role in the formulation. While a lower-viscosity adhesive may lack sufficient cohesive strength to be retained where it is applied, and it may be washed away; a higher-viscosity formulation may not produce sufficient foam to cover the cavity or be fluid enough to reach the tissue. This problem can be particularly important if the adhesive must be applied to wet tissue. In addition, stronger gels or gels that polymerize faster have greater cohesive strength but might not effectively penetrate and interlock with tissue. Thus, the adhesive's flow properties and gel strength is are critical. (19-21).

The sticky, gummy consistency of the agent maintains the foam in situ over lacerated tissue despite the flow of blood, while PVP and other large non-inflammatory molecules enhance the physical adhesion of the foam to wet tissue. The foam property allows for more extensive attachment than would be achievable from a homogeneous liquid form, and also provides a scaffold for the growing fibrin network that binds sundered tissue and forms a barrier to blood flow. The incorporation of a processed bacterial- or plant-derived carbohydrate-based gel component, used as gel enhancer, and depleted of its inflammatory effects—such as alginate or hyaluronic salts or hyaluronic acid, known to form robust hydrogels—is preferably used to enhance the viscoelastic property of the composition (FIGS. 5 and 6). Degraded Iota carrageenan, alginates or hyaluronic salts or hyaluronic acid with sulfate groups or acid are added to better achieve hemostasis in pooled blood without triggering significant inflammatory reaction.

The carbohydrate subunits of carrageenan are preferably connected by $\alpha$-1→3 galactosidic bonds, which do not exist in humans and large apes; consequently, molecules such as carrageenan that contain these bonds are highly immunogenic. The $\alpha$-1→3 galactosidic bond is the major cause of inflammation in carrageenan (44. 45). This chemical group can be removed by degrading carrageenan with cm $\alpha$-1→3 galactosidase.

Fibrin Monomer Polymerization:

An experimental method for producing fibrin monomer was first described and published by Belitser et al (1968, BBA) (34). Such method limits the production of monomer to a few milligrams per day. The preparation, properties, polymerization, and equilibria in the fibrinogen-fibrin conversion, solubility, activation and cross-linking of fibrin monomer has have been studied by several authors since 1968 (35-43). Although U.S. Pat. No. 5,750,657 to Edwardson et al. describes a method of preparing a fibrin sealant utilizing a fibrin monomer composition, the ClotFoam sealant composition, the neutralization of the fibrin monomer to produce a polymer, and the use of fibrin monomer produced by the dialysis method, are entirely novel. U.S. Pat. No. 8,367,802 Falus et al describes a commercially viable method for producing fibrin monomer in solution in industrial quantities.

The composition of parts and method of production of the fibrin monomer are critical to the performance of a non-compressible technology. The power to stick to the lacerated tissue in a pool of blood depends on the cellular and matrix interactions. The characteristics of the fibrin itself, such as the thickness of the fibers, the number of branch points, the porosity, and the permeability and other polymerization characteristics define the interactions between specific-binding sites on fibrin, pro-enzymes, clotting factors, enzyme inhibitors, and cell receptors [24]. Chloride and Zn ions have been identified as modulators of fibrin polymerization; because these ions control fiber size by inhibiting the growth of thicker, stiffer, and straighter fibers.

The pH-studies conducted by other investigators (34) and our own investigations, demonstrated that a pH and ionic strength dependency on polymerization and crosslinking of the scaffold and fibrin monomer—and therefore clot formation—existed. The pH determines the viscosity of the solution comprising the scaffold and the ability of the solution to neutralize the acid pH of monomer solution; thereby producing a polymer that will be stabilized by ACTIVA. Clot foam ClotFoam parts A, B, C and D are formulated to maintain optimal pH to favor the incorporation, preservation and activity of fibrin sealant components; fibrin monomer, and Activa.
Role of the Foam.

The complementary process that allow the compounds to reach the bleeding source or remain at the lacerated site to form a clot, is triggered by an organic non-toxic non-exothermic reaction; producing a sticky foam that spreads throughout the cavity in the same way that sealing foams are use used to repair tires. Sodium monobasic phosphate $NaH_2PO_4$, is used to buffer pH of Solution B to promote foaming when mixed with solution A by acid-base neutralization of the $NaHCO_3$ and Carbomer 934. The volume expansion produced by the foam-triggering component is goes from 300% to 400% of the original volume within 10 seconds of mixing solutions. These time frames, strengths and volumes are convenient in the sense that they allow ClotFoam solutions to generate a foam that is distributed throughout the cavity in the form of a strong gel that adheres (sticks) to the lacerated tissue. Our studies have determined the concentration of components necessary to adjust the gel time and gel phase duration (25).
Role of Divalent Metal Ions.

ClotFoam composition in its present form contains Calcium, Zinc and Magnesium ions. It has been established that these ions can markedly increase the rates of fibrin polymerization, and the length and strength of fibrin filaments. The presence of additional Ca+ and Zinc enhance the progression between the inflammatory response and the coagulation cascade. $Zn^+$ modulates fibrin assembly.
Role of Activa:

This Ca independent transglutaminase enzyme has the double role of crosslinking the gelatin-based polymer and the fibrin polymer.

SUMMARY OF THE INVENTION

The present invention lies within the domain of biological hemostats, adhesives and tissue sealants, which are biodegradable, non-inflammatory and nontoxic; intended for therapeutic use, for example, as an intracavitary hemostatic agent for non-compressible hemorrhage.

In one aspect, the present invention relates to biocompatible non-inflammatory fluid adhesive protein foam as well as to biocompatible fluid/foam adhesive, which is bioreabsorbable and nontoxic, for surgical or therapeutic use. It also relates to such foam containing bioactive substances which can be released in a given site.

In another aspect, the invention relates to a process for producing such an adhesive foam and to a device to deliver such preparation. Extensive in vivo studies show that ClotFoam is an excellent hemostatic agent candidate for emergency situations and combat trauma as well for non-invasive surgical procedures. If needed, it can be applied by paramedics, it is durable, possess minimal risk, require little training to use, is effective against severe bleeding that would otherwise lead to exsanguination, and capable of sustaining hemostasis for at least several hours to permit safe evacuation to definitive care centers. The application through a "mixing needle" specially designed for non-invasive use is safe, and can be performed in the battlefield or in a medical facility. Thus, ClotFoam is a novel concept since there is no other compound that can be delivered through a needle in a minimally invasive procedure, reaching the injured tissue within the abdominal or other cavity through pooled or flowing blood.

BRIEF DESCRIPTION OF THE DRAWINGS

FIG. 8 Strength of fibrin monomer at various temperatures measured by clotting time over a 50-day period
FIG. 9 Microphotography of fibroblast growth in media containing Clot Foam at day-0 (a), 3 (b) and 7 (c) (biocompatibility)
FIG. 10 Livers removed for observation of the lesions and clot forming effect in control animals (a) treated with NaCl and ClotFoam treated (b) showing damaged area is tightly closed.

DETAILED DESCRIPTION

We have developed an intracavitary hemostatic agent in liquid form, CLOTFOAM®, and a method of application for the use in non-compressible hemorrhage outside the operating room or in non-invasive surgical procedures.

Figure 4:
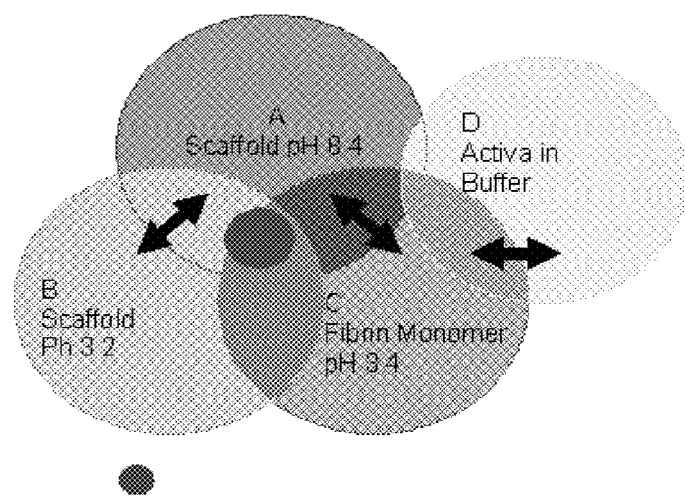

ClotFoam is a novel hydrogel carrying a fibrin sealant, which is designed to promote hemostasis in cases of severe bleeding, to seal tissue and to stop hemorrhage without compression resulting from organ resection, trauma and/or severe intracavitary wounds; or wounds of solid organ, soft tissue or brain that may otherwise lead to clinical complications or exsanguinations. CLOTFOAM® is intended to be used specifically but not exclusively as an hemostatic agent for emergency situations and combat trauma; and for minimally invasive surgical procedures such as laparoscopic surgery and cosmetic surgery. This sealant agent provides hemostasis as well as adhesiveness between surfaces of damaged tissue. ClotFoam is a novel concept since there is no other compound that can be: 1) be delivered through a laparoscopic port or a wound entrance, 2) achieve hemostasis within 10 minutes of application without compression in minimally invasive procedures and sustain hemostasis for one hour in cases of very severe intracavitary trauma, 3) be used when sutures and/or staples are undesirable, inappropriate or impossible; and stop the bleeding and promote early adherence of damaged tissue, and 4) reach the injured tissue within the abdominal cavity through pooled or flowing blood. CLOTFOAM can be used: a) immediately after trauma in the battlefield or at the site of the accident; b) can be applied by paramedics; c) can maintain its viscosity at a wide range of temperatures CLOTFOAM is a composition (FIG. 4.) comprised of four aqueous solutions, that—when mixed and delivered by a pneumatic operating device—form an adhesive 3D-complex hydrogel (scaffold) carrying fibrin monomer; which is polymerized/crosslinked by a reaction with the scaffold, and stabilized by ACTIVA, and by Factor XIII present in the blood.

The process that allows the agent to reach the bleeding source or remain at the lacerated site to form a clot is initiated by the mixture of solutions A, B, C, and D that form a gel. Once the solutions are mixed, they produce a non-toxic low-exothermic reaction that leads to a sticky foam (hydrogel). This foam spreads throughout the cavity in the same way that sealing foams are used to repair tires. The sticky, gummy consistency of the agent maintains the foam in situ over lacerated tissue despite the flow of blood, rapidly forming an adhesive matrix over damaged tissue that 1) seals the wound with a solid cap, 2) triggers the coagulation cascade to form a blood clot by introducing a barrier along the wound, and 3) attaches to the lacerated tissue by a non-covalent action.

The hemostatic properties of CloFoam formulations are based on the physical and coagulation properties of a scaffold (formed by solution A+ solution B); which is mixed with fibrin monomer in acid solution (C), and with ACTIVA (in solution D)—added to which stabilizes stabilize the fibrin polymer. The hydrogel scaffold consists of a mixture of Teleostan Gelatin type A in liquid phase, human serum albumin, Polyvinylpyrrolidone (PVP)—crosslinked by, (but not exclusively so) by Carbomer 934 (polyacrylic acid) in the presence of calcium independent transglutaminase enzyme Activa™; and gel enhancers—such as galactosidase-degraded Carrageenan, or alginate sulfates or hyaluronic acid or hyaluronic salts; and sucrose mixed with a water-soluble foam inducer of sodium bicarbonate and dihydrogen phosphate. Other crosslinking agents are Carboxymethyl cellulose and albumin.

Solution C (containing fibrin monomer dissolved in acetic acid) or sodium acetate is polymerized by pH neutralization pH 7 to 7.2) once it is mixed with solution A (pH 8.4) and then stabilized by solution D (ACTIVA). Ca, Mg and Zn ions, enhance the polymerization reaction.

Figure 2:
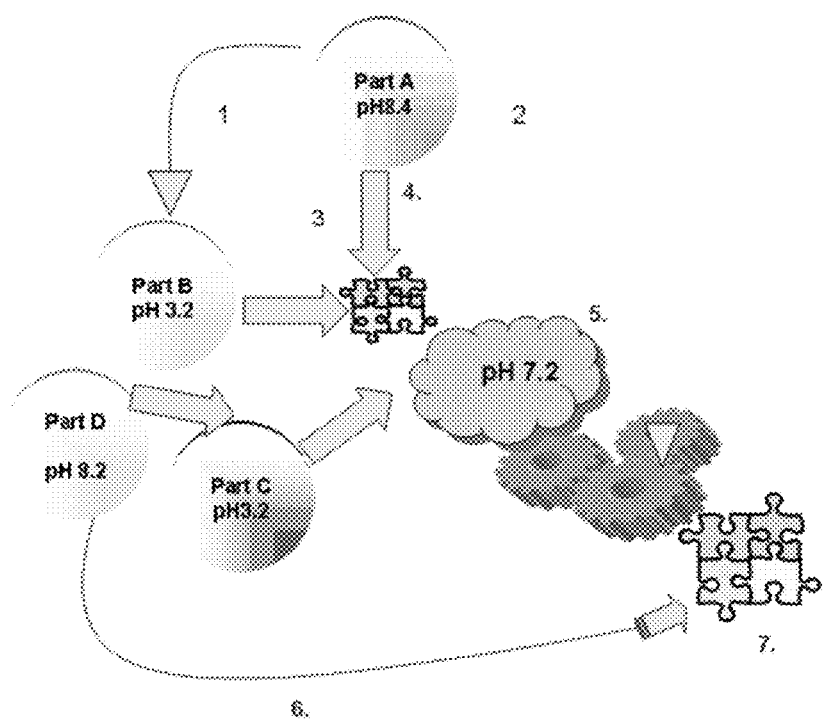

The mechanism of action illustrated in FIG. 2 shows how solution A mixed with solution B crosslinks gelatin and albumin to form a strong foaming (liposomal) hydrgel that expands the original volume by 400%. While the gel is being formed; fibrin monomer contained in solution (C) is polymerized by a change of pH (from pH 3.4 to pH 7.0 to 7.2), or neutralization, by solution A (pH 8.4). Solution D delivers the calcium ions to polymerize the monomer and ACTIVA necessary to stabilize the monomer. The ability to remain at the wound site despite the flow of blood; to form a matrix exclusively over lacerated tissue, and to seal the wound, is achieved through: a) the surface adhesion and viscoelastic characteristics of the foam components, that produces a very sticky matrix carrying the fibrin monomer, and b) the in situ generation of a fibrin polymer, which in the presence of ACTIVA and calcium ions forms a fibrin clot. The four separate solutions are required in order to preserve the activity of components, prevent chemical reactions among them, and maintain the pH before being mixed.

The components that contribute the formation of the foam are: sodium bicarbonate, dihydrogen phosphate, Carbomer 934. The following components provide the physical viscoelastic properties: teleostan gelatin type A in liquid phase, Human serum albumin, galactosidase-degraded carrageenan; or alginate suftate, or hyaluronic salt or hyaluronic acid, polyvinylpyrrolidone, sucrose and Carbomer 934. The complementary presence of additional Ca, Mg and Zinc ions chance the polymerization process.

ClotFoam Formulation.

ClotFoam is produced by the combination of 4 solutions: A,B, C and D

Solution A:

Step 1. Preparation of Neutral A:

micromolar range of ZnCl

Millimolar range $MgSO_4$

Teleostan cold water fish gel sucrose polyvinylpyrrolidone $H_2O$, all contents are stirred to homogeneity and then the solution is neutralized to pH 7.1 with NaOH Step 2. preparation of final solution A Neutral A" (above)

Carrageenan, type 2 or alpha galactosidase-degraded iota carrageean, or alginate sulfate or hyaluronic salt or hyaluronic acid $NaHCO_3$ Human serum albumin All components are stirred, resulting in a suspension, which is then homogenized an Step 3) preparation of Solution B $NaH_2PO_4$ Tris-Base Carbomer 934

Step 4) preparation of Solution C 90-120 mg/ml Fibrin monomer solution in 0.125% ice cold AcOH (pH 3.4) are prepared by dialysis method.

Solution D

ACTIVA dissolved in HEPES buffer and Calcium chloride

All parts are sterilized following a method further described. Endotoxins are removed by filtration over polymixin resin, pressure cooking and UV radiation. Upon mixing of the solutions A and B; Schiff base is formed between the amino groups in the modified (fish) gelatin used in the CLOTFOAM composition—and the aldehyde groups in the modified polysaccharides—which results in intermolecular cross-linking and gel formation. The gel formation can take place within 5 seconds.

ClotFoam gelatin is produced from fish skin, and it is usually referred to as type 'A' gelatin. The raw material for the production of this gelatin is the skin from deep water fish such as cod, haddock and pollock. It is a protein derived by a mild partial hydrolysis from collagen at relatively low temperature. Two of its most useful properties are gel strength and viscosity, on which it is mainly assessed.

The uniqueness of fish gelatin lies in the amino acid content of the gelatin. Although all gelatins are composed of the same 20 amino acids, there can be a variation in the amount of amino acids, proline and hydroxyproline. With lower amounts of these amino acids, there is less hydrogen bonding of gelatin in water solutions, and hence a reduction in the gelling temperature. Gelatin from cod skin gels at 10° C.; whereas gelatin from carp skin would be more similar to animal gelatin, which gels above room temperature. Fish gelatin can be reacted with anhydrides under alkaline conditions, reducing or eliminating the effect of aldehydes as a hardening agent on the gelatin. Boiling hydrolyzes the collagen, and converts it into gelatin. An acid process gives type A gelatin, which can negatively interact with other anionic polymers, a chemical feature that gives ClotFoam its adhesiveness properties to lacerated tissue.

There is also an important relationship between the temperature at which the fish metabolizes and the properties of the skin and the resultant extracted gelatin. Gelatin derived from the skin of deep cold water fish has lower amounts of proline and hydroxyproline; and, as a result, water solutions will not gel at room temperature, but will remain liquid to 8 to 10° C.; while most animal gelatin gels at 32° C. This property is useful to produce a product which has the capability to be stored at room temperature in its liquid physical state. Also, it is important to be able to keep the solubility of the product in a wide range of temperatures in order to be readily to be activated in any environment of battlefield, whether cold or warm weather.

Figure 1:
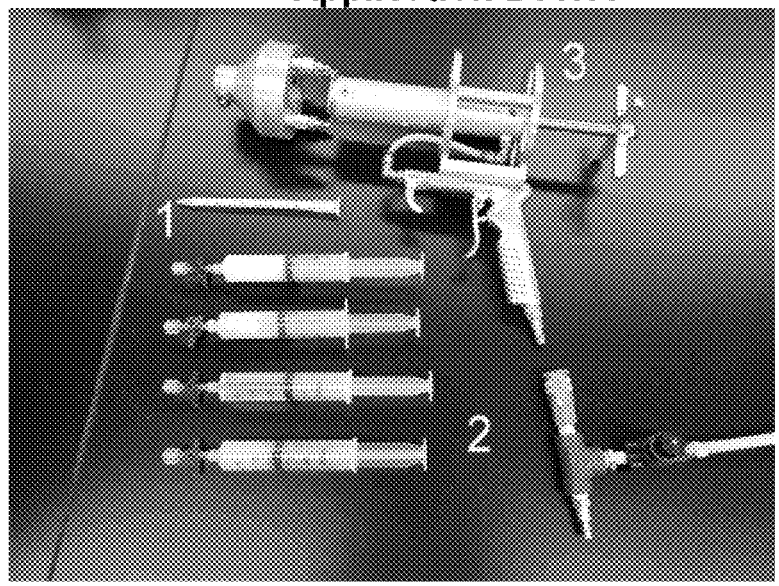
FIG. 1 ClotFoam 4-parts applicator and mixing needle
1—Mixing needle
2—Syringes holder containing the parts
3—Pneumatic piston
FIG. 2. Mode of action of action
1—Part A mixes with Part B to form an hydrogel foam liberating $CO_2$
2—Part C mixes with Part D to polymerize the fibrin monomer and Ca++ to activate
  Factor XIII and transglutaminase enzyme to strengthen cross linking of fibrin polymer
3—$CO_2$
4—Crosslinked gelatin reinforced by fibrin polymer forms a strong gel foam
5—Foam spreads throughout cavity over tissue
6—Activated Factor XIII from blood stabilizes (crosslinks) Fibrin polymer
7—Crosslinked fibrin polymer embedded in scaffold attaches to lacerated tissue
FIG. 3 Graph of intratissular adherence measured in gr./$cm^2$ comparing ClotFoam fibrin monomer technology against the current available sealants made of fibrinogen and thrombin mixed in situ
FIG. 4. Diagram of 4-parts component Interaction
FIG. 5 Rheometry of gel process alginate as a gel enhancer begins within 6 seconds of mixing the liquid solutions, reaching gel strength of 7,000 dyn/$cm^2$±1,000 dyn/$cm^2$ in 10 seconds. Gel state remains stable between 10 to 20 minutes.

Delivery Methods:

ClotFoam is delivered into the cavity by an a hydraulic applicator through a mixing needle (FIG. 1). The mixing needle can be adapted for use in different laparoscopic procedures as for other minimally invasive procedures.

EXAMPLES

1. Adhesion and Viscoelastic Properties

The adhesion characteristics to vital human tissue and the kinetics of polymerization of the gel have been tested in in-vitro and ex-vivo studies.

1.1. Adhesion properties

Adhesion and tensile measurements (Intratissular adherence and clot strength) were conducted in Sprague-Dawley rats' liver tissue. The liver was chosen because is the most frequently damaged organ in intraperitoneal trauma, followed by the spleen. Experimental Models Sprague-Dawley rats (250 to 300 g) were anesthetized. The abdominal cavity was approached medially; and the liver was completely dissected out and excised. The liver was chosen because it is the most frequently damaged organ in intraperitoneal non-compressible hemorrhage followed by the spleen. We conducted adhesion and tensile studies with an isometric transducer.

Figure 3:
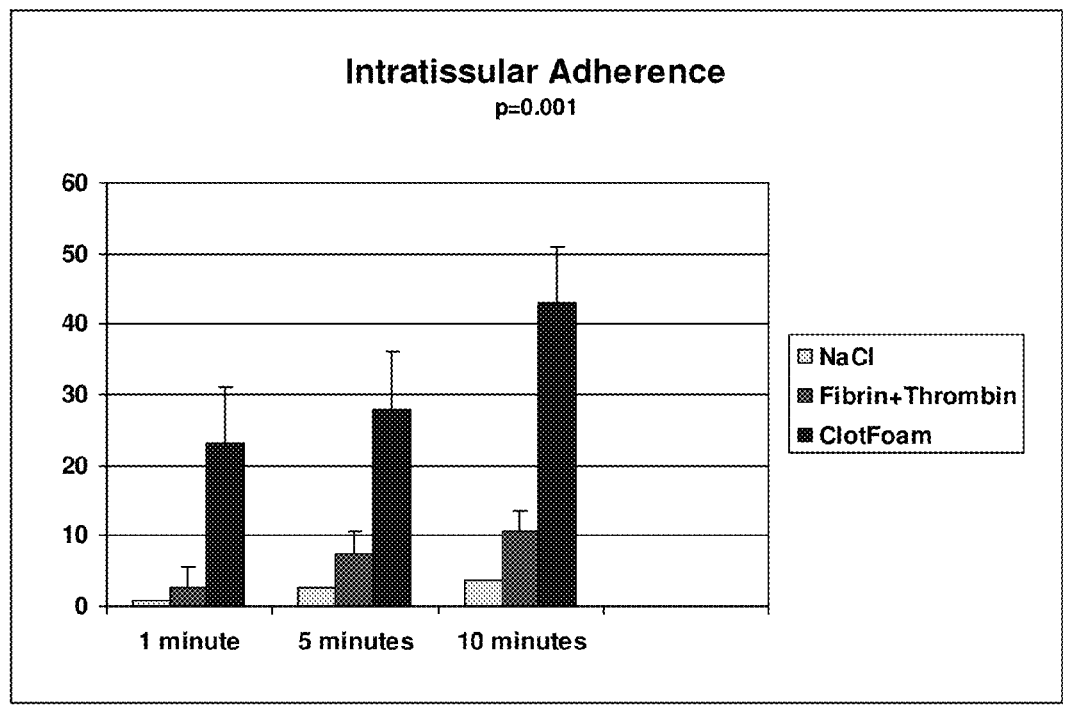

1.1.1 Tensile Measurements:

The two largest lobes separated. One lobe was attached to a holder that was fixed later to the isometric transducer. The other lobe was placed in a flat bed of gauze in a container that could gradually be elevated and lowered to produce contact with the piece of liver in the transducer's holder. A damage area of 1 cm$^2$ was produced in both liver pieces. The formulation to be tested for tissue adherence was deposited between the two pieces. The specimens were placed in contact at a baseline pressure of 0 gr. At various time points (1, 5 and 10 minutes of exposure and contact), the pressure needed to completely separate them was recorded. We tested the current formulation and compared these results with a solution of NaCl as controls and with standard technique used by all available fibrin sealants which mix thrombin and fibrinogen in-situ. The results of the intratissular adherence are depicted in FIG. 3 The force of adherence induced by ClotFoam after 10 min is more than 200% stronger than the control in the intratissular adhesion secondary to the exposition of damaged tissue to the foam.

Adhesiveness was measured in gr/cm$^2$. All tests were performed at 37° C.

1.1.2 Quantification of Clot Strength:

To study the strength of the formed clot under the influence of the CLOTFOAM, we used the following experimental model: Blood was collected in a test tube previously prepared to contain a strand of cotton suture with a piece of cotton gauze as a weight in one end, to maintain that side on the bottom of the tube; and at the other end out of the tube with a loop to hang the strand to the isometric transducer. The strand of cotton suture was included in the blood and allowed to coagulate for 2 minutes. The other end of the strand was fixed to an isometric transducer, and then pulled down to measure the force (in grams) necessary to pull up the strand from the clot and test tube. Clot strength observed in three experimental groups that included: blood plus saline solution (B+S), blood alone (BA), and blood with the CLOTFOAM (B+Gel). showed a statistically-significant (P=0.001) difference when the blood was treated with CLOTFOAM as compared to blood alone or blood plus saline.

1.2. Viscoelastic Properties Amid Gelation

The viscoelastic properties of the cross-linked polymer pairs forming a gel are critical to improved crosslinking chemistries (e.g, Calcium-independent transglutaminase enzyme) and e) more controllable polymerization reactions.

Rheological studies were performed to compare the viscoelastic profiles of ClotFoam formulation amid gelation with various combinations of materials currently used to produce surgical sealants. Gelation studies were conducted with a parallel plate geometry; all samples were transferred immediately after mixing (time t=0), and measurement started at t=6 s. For time and stress sweeping tests, storage moduli (G') and loss moduli (G") were monitored as a function of time at a 5 Hz frequency and a 2% stress strain at 37° C.

Rheological measurements of ClotFoam composition were compared to:
 a) Gelatin, PVP
 b) Gelatin Poly(L-glutamic acid)
 c) Chitosan, alginic acid
The following crosslinking catalyzers
 a) Calcium-independent transglutaminase enzyme mTg
 b) EDC
 c) Carbomer 934
Alternative materials:
 a) Carboxymethyl Cellulose
 b) Acrylates
Gel enhancers:
 a) Galactosidase depleted Carrageenan
 b) Alginate sulfate
 c) Hyaluronic sulfate The gelation kinetics and morphological evolution that is considered optimal for this application is rheologically described by:

a) the intersection of G' and G" (crosslinking and change of state from liquid to gel) within 10 seconds following the mixing of components;
b) the rapid increase in the value of G' over 6000 dyn/cm$^2$ pointing to a strong gel (FIG. 5 and FIG. 5);
c) maintenance of a high value of G' for over 10 minutes and decrease of G" after 10 minutes that return the agent to a liquid state facilitating its absorption by the cavity fluids; and a tangent value increasing from 0.1 to 0.4, indicating an increasing storage energy over released energy.

Figure 5:
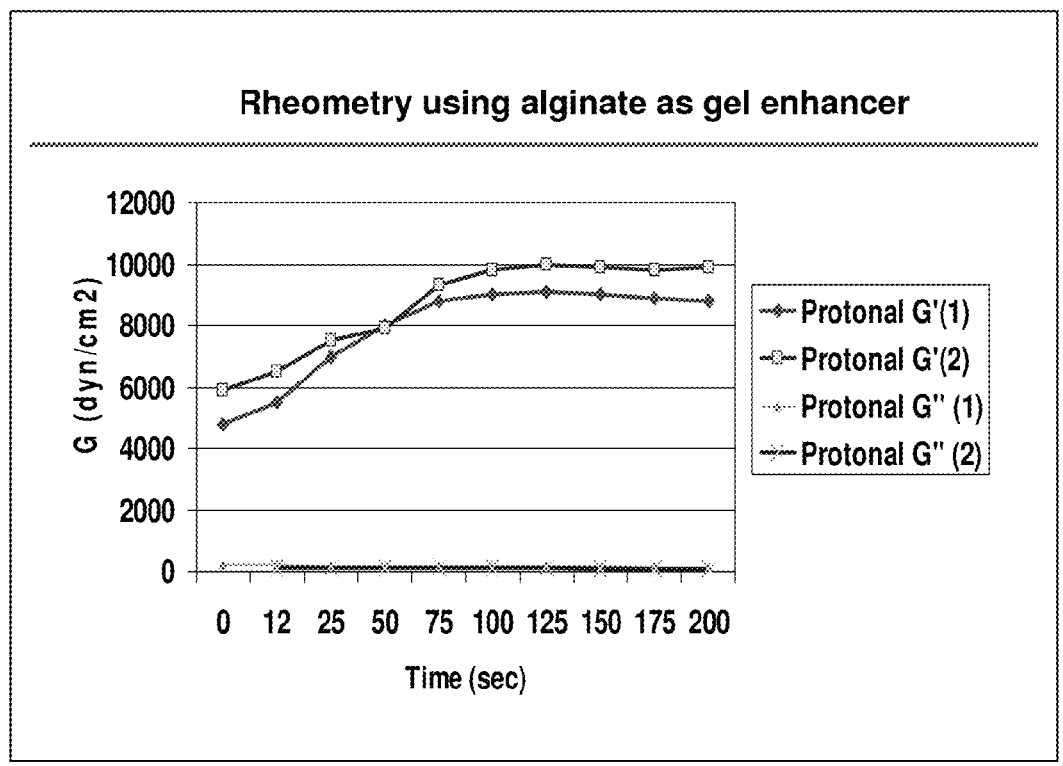
Figure 6:
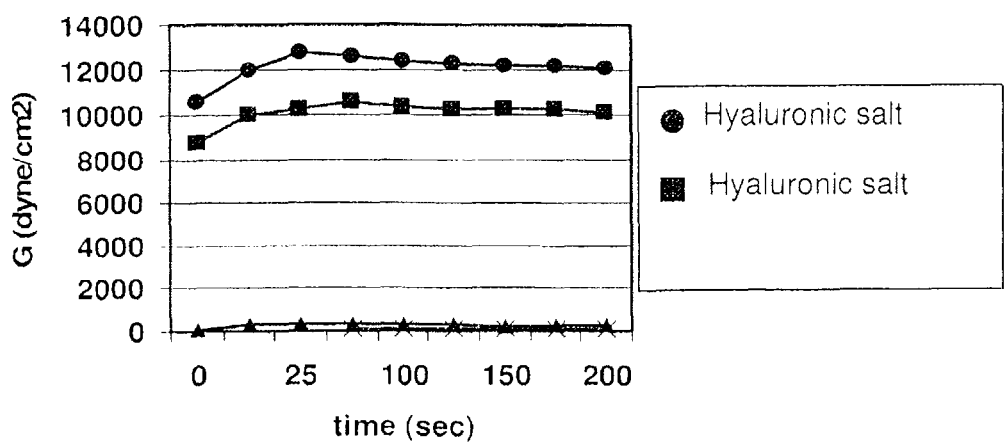
FIG. 6. Rheometry with incorporation of hyaluronic salts, with high Ca Concentration.
Figure 7:
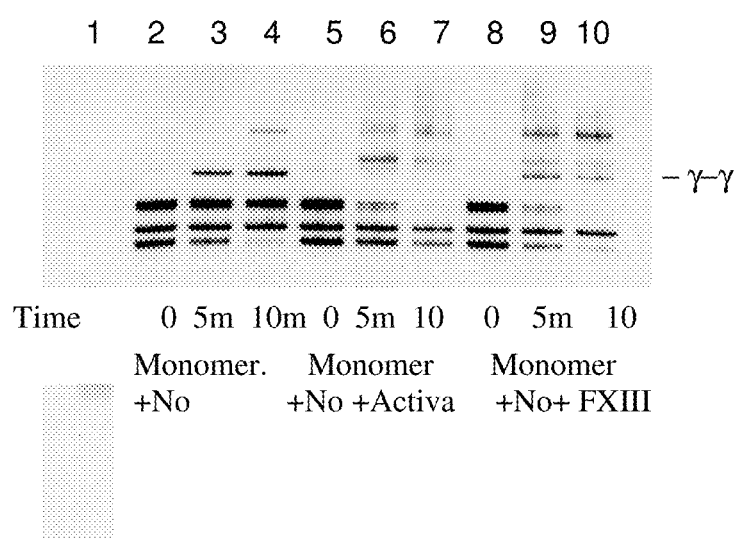
FIG. 7 fibrin monomer polymerization over a 30 to 46 day-storage period.
Figure 10:
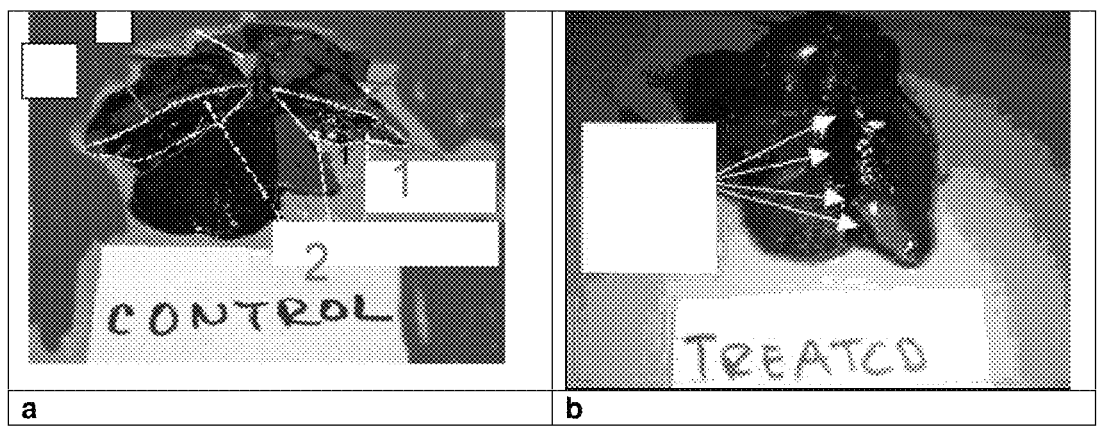

FIG. 5 shows the gel strength when Carbomer is used as crosslinking agent of gelatin in the presence of Human Serum Albumin in the current formulation with alginate sulfate as gel enhancer. Rheological measurements of the current formulation indicate that the composition using these combinations catalyzes the conversion of gelatin solutions into very strong hydrogels, and gel times are on the order of 6 seconds. G' reaches 7000 dyn/cm$^2$ in less than 20 seconds, while G" remains bellow 2000 dyn/cm$^2$ 1.3. Studies on the Effect of Divalent Metal Ions The effect of $Ca^{2+}$, $Zn^{2+}$ and $Mg^{2+}$ on the effectiveness of gel, were investigated. It has been established that these ions could increase foam expansion, accelerate gelatin crosslinking, fibrin polymerization, and both enhance the length and strength of fibrin filaments as well as the gel strength.

Characterization of the kinetics is of utility as it may indicate that though a given metal ion addend could enhance gel strength, and drastically decrease cross-linking time of the various polymers included in the 3-D structure.

Ion testing with Magnesium Chloride and Zinc Chloride-Solutions were made using the original baseline formulation. Ions were added as follows: 20 µM ZnCl2 solution, a 20 µM MgCl2 solution, a 40 µM ZnCl2 solution, a 40 µM MgCl2 solution, a ZnCl2 solution, and finally a 60 µM MgCl2 solution by adding 0.002 M ZnCl2 and 0.002 MgCl2 solutions.

The change in gel strength as a function of time was tested by rheometry in the absence of divalent metal ions to establish baselines; followed by adding metals ions at various concentrations that produce maximum effects on clot strength. Concentration of 20 µM and less of $Zn^{2+}$ increased gel strength by an estimated 15%-20%, and decreased the gel time, as observed by the slope of G' and G""—and enhanced the adhesiveness of the scaffold; which was estimated by a tactile observation using latex gloves. Tests for displacement were performed using a 50 mL graduated cylinder. Results: The 20 µM MgCl2 solution showed the best improvement in volume displacement and adhesive strength.

2. Foam Volume Expansion

An analytical method for determination of foam volume expansion was devised and validated. Optimal volume expansion of foam was achieved with the addition of metallic ions and acrylic acids, by alterations of the initial pH values of the two constituents. The volume varies from 400% to 500% expansion.

The formulation incorporates biocompatible agents that produce foam both by means of chemical reaction. The foam producing approach is harmless and avoids putting tissues in contact in microenvironments with solutions that breach the extremes of physiological pH that gives rise to undesirable irritation and adhesions.

Methods:

The foaming capacity was quantified by measuring bulk volume, after polymerization, of a known weight of reactants, as displacement by gel in a volume of inert solvent such as hexane or $CCl_4$. This value was compared to a control formulation, based on bicarbonate and acetic acid.

Each sample was tested 3 times. 1 mL of solution A was simultaneously added to 1 mL of solution B in a 16×100 mm test tube using two 1 mL disposable BD syringes. Each mixture was vortexed for 5 seconds immediately after mixing. Displacement tests were performed 20 minutes after vortexing, and were tested using the highest point of foaming marked by a Sharpie® on the test tube. The test tube was lowered into a 50 mL graduated cylinder containing 40 mL of acetone until the bottom of the meniscus of the acetone was aligned with the Sharpie® mark and the displacement in mL was noted. Stickiness tests were performed 40 minutes by shear test after vortexing, to ensure the solutions had reached their heightened adhesiveness.

3. Fibrin Polymerization

We conducted molecular chemistry assays (SDS PAGE and Western Blot) to determine the effectiveness of fibrin monomer in solution (C) polymerization when pH is neutralized (7.0-7.2) by solutions A and B. We also compared the stabilization of the fibrin polymer with ACTIVA versus factor XIII.

3.1. Polymerization of Fibrin Within the ClotFoam Gel

To test the polymerization rate of the fibrin monomer in ClotFoam when neutralized by A and B), and to determine the effect of stabilization by transglutaminase enzymes and FACTOR XIII, we conducted western blot assays using anti-fibrinogen antibody. The chains of fibrin polymers were detected by the reaction with polyclonal sheep anti-Human Fibrinogen (Fg) affinity purified peroxidase conjugated antibody. (Cat #: SAFG-APHRP, Enzyme Research Laboratory, IN) for 1 hr (1 part in 50K 5% milk in TBST).

The polymerization of fibrin when all four solutions of ClotFoam composition are mixed in the presence either of FXIII or ACTIVA and $Ca^{2+}$ is established by the western blot essay shown in. Both enzymes catalyzed fibrin monomer conversion to a stable insoluble fibrin clot.

4. Shelf Life 4.1 Shelf Life of Monomer Part in Solution C

The purpose of these experiments was to establish that monomer does not degrade over time and under refrigerated conditions (4° C.). Fibrin monomer was prepared by dialysis of fibrin polymer against 1 liter of 0.125% acetic acid for 20 h with two changes of the dialysis solution (each in 1 h). Fibrin monomer was concentrated to 17.6 mg/ml. Final yield—80%. Fibrin monomer was then divided into 3 portions, one was kept at 4° C., the other two, one of which contained sodium azide, were kept at room temperature (22° C.); samples for the analysis have been withdrawn at the indicated time. The shelf life of Fibrin monomer was analyzed by SDS-PAGE and stained with Imperial Protein Stain (ThermoScientific). The analyses of these samples were performed after 1, 4 and 15 days and compared with the Fibrin monomer samples obtained by independent method (Medved & Oglev, unpublished data) and stored for over 30 days at 4° C.

4.2. Clottability

SDS-Page data show that there was no visible fibrin degradation over time—neither at 4° C. nor at 22° C. Clottability studies by the absorption method show that the monomer maintains stability over 6 weeks, while at 22° C., stability is maintained over one week.

Conclusion: the fibrin monomer produced by either method described in this patent can be stored at 4° C. for over 60 days. (FIG. 8)

5. Sterilization

Sterile preparations of ClotFoam were studied. The Neutral Half of PART A was sterile filtered in a biological safety cabinet using a Nalg-Nunc 500 mL device (Cat #450-0045, nitrocellulose membrane, 0.45 m filter).
Solution A: albumin, $MgCl_2$ and $CaCl_2$ were dissolved in sterile water, and were added in 0.15 g solution. The solution was sterile filter filtered using 0.22 μm Millpore Syringe filter into above 8 mL of Neutral part. To this mixture then was added premeasured and autoclaved sterile 1.2 g of solid $NaHCO_3$ and 0.4 g of Carrageenan.
Solution B: sodium monophosphate, tris(hydroxymethyl) aminomethane (TRIS-Base) and Activa™ were dissolved in sterile water. The solution was sterile-filtered using 0.22 μm Millpore syringe filter. To this sterile mixture, 0.5 g UV sterile Carbomer was added.
Solution C: The acidic Fibrin Monomer was sterile filtered in a biological safety cabinet using a Nalg-Nunc 500 mL device (Cat #450-0045, nitrocellulose membrane, 0.45 m filter).
Solution D: ACTIVA dissolved in buffer solution was sterile filtered in a biological safety cabinet using a Nalg-Nunc 500 mL device (Cat #450-0045, nitrocellulose membrane, 0.45m filter).
Growth Study:

The general experimental protocol included preparation of sample solutions which were then plated on potato dextrose agar (PDA, Sigma-Aldrich, Cat # P2182) and tryptic soy agar (TSA, Sigma-Aldrich, Cat # T4536) gels in Petri dishes for growth. The PDA and TSA gels were incubated and observed at the indicated periods of time for colony growth (mold and/or bacteria) at 37° C. and evaluated for colony growth using the naked eye at established time periods. Multiple samples are indicated with a 1, 2 and 3 designation in data tables.

TABLE 1

| Colony Count Key | |
|---|---|
| Symbol | Count |
| − | No visible growth |
| + | 1-199 visible colonies |
| ++ | 200-399 visible colonies |
| +++ | >400 visible colonies |

Table 2. Results of studies of microorganism growth analysis on PDA and TSA of the sterile ClotFoam solutions.

TABLE 2

| | | Sterilization Studies by Bacterial Growth on PDA/TSA at 37° C. | | | | | | | | | | | | | |
|---|---|---|---|---|---|---|---|---|---|---|---|---|---|---|---|
| | | Potato Dextrose Agar (PDA) | | | | | | | Tryptic Soy Agar (TSA) | | | | | | |
| Time Elapsed (days) | | 1 | 2 | 3 | 4 | 5 | 6 | 7 | 11 | 1 | 2 | 3 | 4 | 5 | 6 | 7 | 11 |
| Sample | # s$ | | | | | | | | | | | | | | | | |
| Neutral Half* | 1 | — | | | — | | — | — | | | — | | | — | | — | — |
| A**^ | 1 | — | | | — | | — | — | | | — | | | — | | — | — |
| | 2 | — | | | — | | — | — | | | — | | | — | | — | — |
| | 3 | — | | | + | | — | — | | | — | | | — | | — | — |
| B**^ | 1 | — | | | — | | ! | — | | | — | | | — | | — | — |
| | 2 | — | | | — | | — | — | | | — | | | — | | — | — |
| | 3 | — | | | — | | — | — | | | — | | | — | | — | — |
| C** (Fibrin/AcOH, pH 3.5) | 1 | — | | | — | | — | — | | | — | | | — | | — | — |
| | 2 | — | | | — | | — | — | | | — | | | — | | — | — |
| | 3 | — | | | \! | | — | — | | | — | | | — | | — | — |
| Autoclaved $NaHCO_3$+ | 1 | — | | | — | | — | — | | | — | | | — | | — | — |
| | 2 | — | | | — | | — | — | | | — | | | — | | — | — |
| | 3 | — | | | — | | — | — | | | — | | | — | | — | — |
| Autoclaved Carrageenan++ | 1 | — | | | — | | — | — | | | — | | | — | | — | — |
| | 2 | — | | | — | | — | — | | | — | | | — | | — | — |
| | 3 | — | | | — | | — | — | | | — | | | — | | — | — |
| Part D | 3 | — | | | — | | — | — | | | — | | | — | | — | — |

*Neutral Half is sterile filtered using 0.45μ filter, stored for a week at 4° C.
**"sterile" A, B, C used for animal studies in SUNY, stored at 4° C. for a week
^add 1000 μL of sterile water only in A & B to make "liquid"
+Test Sterility of NaHCO3 (used in A) after autoclaving at 121° C. for 20 min, make a saturated solution in sterile water
++Test Sterility of Carrageenan (used in A&B) after autoclaving at 121° C. for 20 min, make a solution in sterile water
$Experiments were performed in triplicates except for Neutral Half
!Experimental error The growth data indicate that Neutral Half and other sterile components yielded no significant growth even after 11 days. Additional sterilization methods with preservatives were tested at different concentrations to inhibit growth. The growth data also indicate that after 3 days, methyl 4-hydroxybenzoate and Germaben II provide sterilization/inhibition of growth.
Conclusion:

Adopting a sterile preparation method inhibits growth of contaminants (mold and bacteria) and may provide an acceptable shelf-life of a commercial product. The addition of preservatives displayed inhibition of microbial growth.

6. Inflammatory Properties

Iota Carrageenan is one of the optimal gel enhancers that allow the composition to achieve hemostasis in severe bleeding conditions without compression. Iota carrageenan contains the α-1-3,6 galactosidic bond, which is the major cause of inflammation—as is shown in animal experiments described below.

Carrageenan is preferably converted into a non-inflammatory compound by enzymatically removing the α-1-3,6 galactosidic bond using α-1-3,6 galactosidase enzyme. The removal by digestion with the α-1-3,6 galactosidase is established by tagging carrageenan with a fluorescent component such as fluorescein, which binds to the α-1-3,6 galactosidic bond. Then both fluorescent carrageenan and digested fluorescent carrageenan are preferably dialyzed against water in order to remove any of the digested off fluorescent or the otherwise unbound fluorescein. Finally the samples are preferably lyophilized to remove water in order to prevent error from having differing amounts of water. Then the various carrageenans are mixed into the ClotFoam solutions: 1. Normal carrageenan, 2. flourescent labeled carrageenan 3. Fluorescent labeled carrageenan that has been digested by α-1-3,6 galactosidase; they are compared in regard to their gelling properties.

To show complete lack of inflammatory response, in addition to the fluorescence test, we conducted an animal study in the swine model. ClotFoam was applied to a 3 cm liver resection produced in the swine model. Four compositions of ClotFoam were compared to controls in a 35-day survival model. The ClotFoam compositions differed by the type of Gel enhancer used as follows:
Group 1: Containing Iota Carrageenan
Group 2: Containing Iota carrageenan depleted by alpha galactoside enzyme
Group 3. Containing Alginate sulphate
Group 4: Containing Hyaluronan sulphate The control group consisted of animals whose wound was sutured as a sole method of hemostasis treated with saline solution. Animals were euthanized at day 35 following resection; and gross necropsy was conducted, as well as a microscopic pathology assessment.
Results:
Group 1: (n=5). Grade 5 adhesions, spread granulomas and inflammatory reaction All pigs in this group had small, raised nodules on various organs in the abdomen, particularly around the injury site associated with the test article. In 50% of the pigs in this group, the nodules were located just around the injury site. Also, multifocal areas of granulomatous inflammation with variable fibrosis were present along the serosal surface and in the hepatic parenchyma. In two of the five animals, the inflammation spread to the spleen, omentum and peritoneum. Correlating microscopic findings for the adhesions were adhesions comprised of fibrous connective tissue; and, for the nodules, multifocal areas of granulomatous inflammation and fibrosis. Contained within the inflammation were accumulations of lightly eosinophilic to amphophilic material that was occasionally rimmed by degenerating neutrophils and mineralization.

Group 2: (n=5). Only two pigs in this group had no nodules around the injury site and mild adhesions associated with the test article. No areas of granulomatous inflammation were present outside of the injury area. Correlating microscopic findings for the adhesions were adhesions comprised of fibrous connective tissue; and, for the nodules, the inflammations were accumulations of lightly eosinophilic to amphophilic material. No mineralization was observed.

Group 3: (n=5). Three of the pigs in this group had no nodules around the injury site and mild adhesions associated with the test article. Microscopic findings were similar to those observed in group 2.

Group 4: (n=5). Results were similar to those observed in group 3.7 Microscopic finding findings were similar to those observed in group 2.
Conclusion:

Evaluation of the inflammatory reaction of ClotFoam with various gel enhancers applied over the injured liver of pigs at 35±2 days following surgery resulted in adhesions and nodules affecting the abdominal organs, grossly. Microscopic findings at the liver injury site included granulomatous inflammation, adhesions, and fibrosis. Extended multifocal areas of granulomatous inflammation extended to other organs, with necrosis; and mineralization was observed only in animals treated with ClotFoam containing non-treated iota carrageenan. Animals treated with ClotFoam containing galactosidase-treated carrageenan, alginate sulfate of or hyaluronic salts produced a similar inflammatory reaction to that observed among control animals. The adhesion scores are significantly higher in group 1 than in other groups.

6. Biocompatibility

Two ClotFoam preparations with and without Sodium Benzoate, prepared under sterile Conditions, were tested. These preparations were tested for biocompatibility with human fibroblasts (HF) and human epithelial cells (A549 cell line, ATCC). Normal human fibroblasts (HFs) were obtained from a commercial source; and cultures established in 60 mm tissue culture plates in Dulbecco's modified Eagle's medium, supplemented with 10% fetal bovine serum and maintained at 37° C. in a humidified 5% $CO_2$ atmosphere ($CO_2$ incubator). Human epithelial cell line A549 was maintained in Minimal Essential Medium supplemented with 10% fetal bovine serum and 2 mM glutamine. When fibroblast and epithelial cell cultures reached subconfluence; control and sodium benzoate ClotFoam preparations were mixed, and immediately delivered into individual dishes. The cultures were returned to the $CO_2$ incubator and examined at day 0 (FIG. 9a), at day 3 (FIG. 9b) and at day 7 (FIG. 9c). ClotFoam material and medium were removed from all cultures, and adherent cells were stained with crystal violet (0.1% in 2% ethanol).

The main observation was a total absence of damage or toxicity to the cells, and absence of any bacterial or fungal contamination. In human fibroblast cultures exposed to ClotFoam preparations, the cells appeared slightly larger or more spread out than in control untreated cultures. Conclusion: ClotFoam and ClotFoam+preservative benzoate are biocompatible; and do not affect, but rather stimulate, the growth and differentiation of cells—which is an important attribute in wound healing agents.

7. Efficacy Experiments in Animal Models

We conducted studies on several intracavitary trauma models on rats and swine (pig) models.
7.1. Effect of ClotFoam on Blood Loss After Grade IV Liver Injury (Rat Models)

Methods: Ten male Sprague-Dawley rats (225-250 g) were used (approved by the Institutional Animal Care and Use Committee of UMB).
Experimental Procedure:

A laparotomy was performed; Grade III liver injuries were induced in the larger left and right lobes. The injury was induced by clamping on both lobules with a hemostatic clamp, and causing injury of the parenchyma of the liver through the two medial lobes.

After the first penetration of the liver, the clamp was opened and repositioned to the animal's left; inducing the second lesion, including more than 40% of the distance from the border to the suprahepatic vena cava. After this repositioning, the liver was penetrated a second time. Further documentation of the liver injury was achieved by excision and inspection of the liver at the conclusion of the experiment. The injuries were through and through. No concomitant damage to the common bile duct, caudal vena cava, or hepatic artery was noted. Ten animals received injuries for this study, and they were assigned randomly to receive either 4 ml of saline solution (Control) or 4 ml of ClotFoam agent.

Immediately after the injury was induced, ClotFoam or saline was administered through a needle into the peritoneal cavity. The bleeding time was observed and recorded. Then the abdominal cavity was closed with 4-0 nylon to observe the animals for 90 minutes. After this period of time the animal was re-anesthetized and all the fluids in the abdominal cavity were collected in a pre-weighed gauze and then re-weighed to measured the intraperitoneal volume and calculate blood losses.

Results:

Bleeding time in the control group showed a mean of 37 seconds (+SD 7.5). In the CLOTFOAM treated group, bleeding in injured areas stops areas within 4 seconds (+1.0). This difference showed statistical significance with p<0.008. Blood loss measurements in the control untreated group were 2.45 mL (from 1.86-3.61) with a SD of 0.67 in the control group. In contrast, the treated group had a mean of 0.95 mL (0.72-1.78) with a SD of 0.55, T-test showed this difference to be statistically significant, with a p value of 0.028.

7.2. Validation of Sealing Efficacy of ClotFoam in Liver Damage (Rat Models)

Livers were removed for observation of the lesions and clot forming behavior. It was found that in controls (FIG. 13) the damaged areas develop some clots on them; but, invariably, they remain separated. In contrast, when the ClotFoam is administered, livers show the formation of very strong clots in the injured areas (FIG. 14), with no adherence of the clot to the undamaged tissue.

7.3. Aortic Model in Laparotomy Experiments

Methods: In this model, a midline laparotomy is made. The aorta is clamped just below the renal arteries and just above the bifurcation of the iliac arteries, effectively gaining infrarenal proximal and distal aortic control. The infrarenal aorta is then pierced with a 25-gauge needle once on both left and right sides of the vessel. After 6 seconds of uncontrolled bleeding, 500 microliters of ClotFoam is applied diffusely throughout the intraperitoneal cavity. After completion of foam application, time to hemostasis is measured. The abdomen is then closed.

Immediately after injury, the rat is given Ringer's solution to maintain mean arterial pressure at about 70-80% of initial MAP (if possible), which is the current standard resuscitation technique for trauma patients. The rat is observed for 20 minutes. After 20 minutes, the animal is re-explored through the same midline incision. All of the blood is collected with pre-weighed gauze pads and total blood loss is calculated Results:

Seventeen animals underwent aortic injury. Animals were randomized into 2 different groups: treated and non-treated with ClotFoam. Survival was 100% at 60 minutes for all animals treated with ClotFoam. No animals survived the injury in the no-treatment group. All pre-injury MAP were similar. Table 4-3 below summarizes the outcomes measured in each group.

TABLE 3

Comparison of outcomes for aortic-injured animals treated with ClotFoam versus no treatment. Resuscitation index is defined as the resuscitation MAP percentage of pre-injury MAP. P values for all outcomes and all formulations are <0.001 compared to no agent.

| Outcome | ClotFoam N = 10 | No Treatment (N = 7) |
|---|---|---|
| Time to hemostasis (s) | 12.2 ± 2.9 | N/A |
| Total blood loss (ml) | 5.2 ± 0.5 | 16.3 ± 0.3 |
| Resuscitation index (%) | 68.8 ± 14.0 | 26.8 ± 2.4 |
| Resuscitation volume (ml) | 12 ± 4.5 | 20.3 ± 2.5 |
| Survival (min) | 60 ± 0 | 18.3 ± 2.9 |

7.4. Cava Vein Model

The second model is a liver/vena caval injury model. In this model, a small upper midline laparotomy is made. The left lobe of the liver and the vena cava are exposed and isolated. A small incision is created in the right lower quadrant, and the ClotFoam applicator tip is placed through that incision; so that the opening is intraperitoneal but remote from where the injury will take place. Next, the injury is created by sharply transecting the left liver lobe and then creating a stab injury into the vena cava. The mini-laparotomy incision is rapidly closed with staples. ClotFoam is then injected into the closed abdominal cavity. Resuscitation, observation and blood loss measurements are collected, as mentioned above.

Twelve animals underwent liver/vena cava vein injuries. Animals were nrandomized into different two groups: treated and untreated with ClotFoam. Survival was 100% at 60 minutes for all animals treated with ClotFoam. The applicator was placed into the intraperitoneal cavity. At the 20 minute mark after liver/caval injury, the animal was opened fully to expose the injured area. The animals in the no treatment group died at >18 minutes from injury. All pre-injury MAP were similar. Table 4 summarizes the outcomes measured in each group.

TABLE 4

| Outcome | ClotFoam (N = 7) | No agent (N = 5) |
|---|---|---|
| Total blood loss (ml) | 3.6 | 14.7 |
| Resuscitation index (%) | 88.6 | 54.3 |
| Resuscitation volume (ml) | 10 | 16 |
| Survival (min) | 30 | 18 |

7.5 Summary of ClotFoam Effects in Three Different Hemorrhagic Models:

Data in table 5 compares results with the different models. Control represents puncture model with NS treatment alone. Numbers represent blood pressure and mean arterial pressure (MAP—in parenthesis) at baseline 10 seconds, 10 minutes and two hours post insult. NS—normal saline administration in ml. NA—not applicable (control animals died before 2 end point). TTH—total time to hemostatsis, measured as a function of a sustained and maintained rise in blood pressure and MAP of 70.

TABLE 5

Comparison of results between protocols

| Model | baseline | 10 sec | NS (ml) | 10min | 2 Hrs | TTH | Survival |
|---|---|---|---|---|---|---|---|
| Aortic | 151/110 (120) | 38/31 (34) | 4.0 | 133/124 (110) | 131/117 (124) | 3 m | all |
| Cava Vein | 140/105 (115) | 63/34 (41) | 3.5 | 109/69 (83) | 130/72 (97) | 2 m | all |
| Liver Injury | 162/102 (128) | 66/41 (50) | 4.2 | 131/69 (87) | 135/87 (102) | 2 m | all |
| Control cava vein | 150/112 (128) | 50/37 (41) | 9.7 | 75/38 (48) | NA | NA | none |
| Control Aortic | 153/108 (119) | 42/34 (33) | 10.5 | N/A | N/A | N/A | none |

7.6. Non-GLP Studies in Pigs

ClotFoam was evaluated in the pig model.

Figure 11:
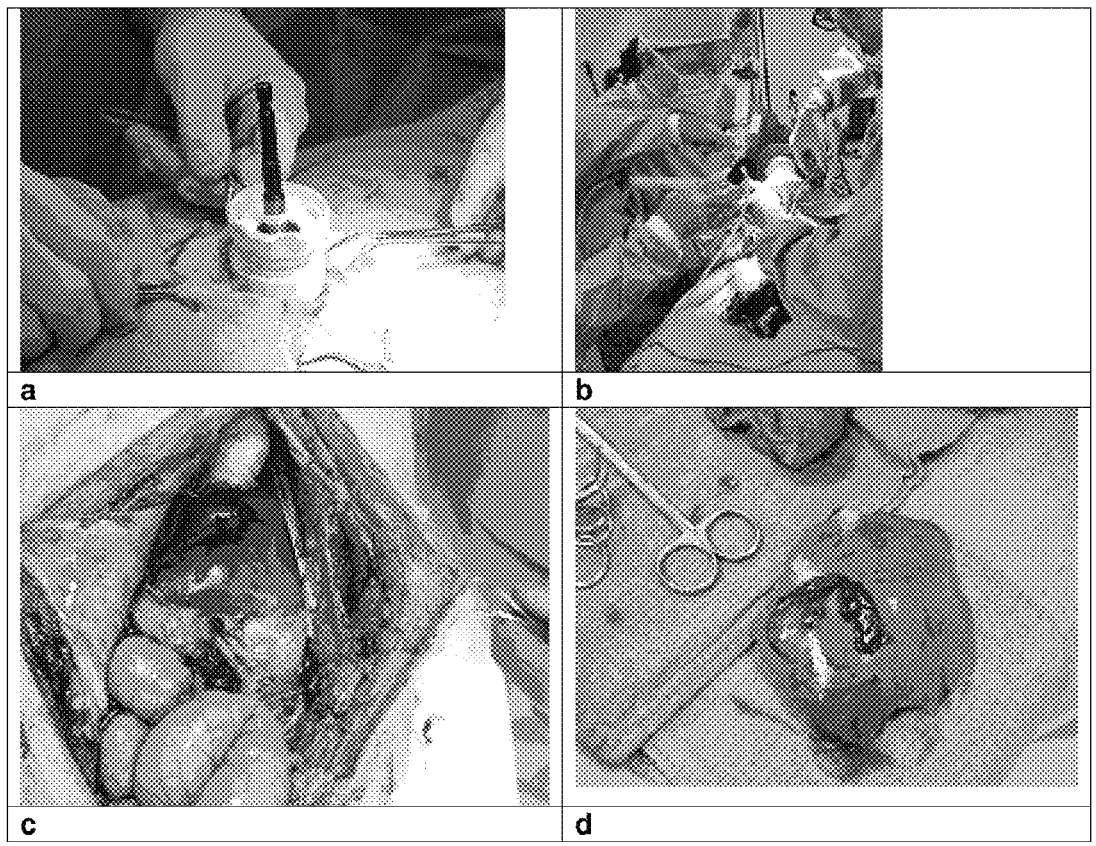
FIG. 11 Grade IV liver injury produced by a drill through a laparoscopic procedure and closed cavity ClotFoam application (pig model). (a) Blind application of the 4-part ClotFoam through the port. (b) Opening the cavity after 60 minutes, (c) showing the clot formation and bleeding control. (d) Measurement of the blood clot and strength.

Methods:

Eighteen female Yorkshire crossbred swine, age 2.5 months, weighing 37±2 kg were used. The protocol was approved by the Institutional Animal Care and Use Committee. Animals then underwent either grade 4 liver injuries via open laparotomy or by laparoscopy. For the purposes of this model, a grade 4 liver injury was a 10 cm deep parenchymal injury with a specially designed high-speed drill with a cutting drill bit creating an injury akin to a penetrating gunshot (GSW) (FIG. 11a). These injuries were consistent with the American Association for the Surgery of Trauma Organ Injury Scaling system.

After the liver was exposed, a spot in the middle of the liver was selected to produce the liver injury. The position was calculated by approximation to the suprahepatic vessels and some branches of the portal vein. The spot was marked with a marker. After the damage was induced, surgeons closed the cavity, and allowed for 30 seconds of massive bleeding before applying ClotFoam through a small perforation. Animals were randomized into 4 groups to date. Group 1 (n=5) consisted of animals who underwent grade IV liver injuries through an open midline laparotomy and had open cavity ClotFoam application. In this group the agent was visually directed to the liver injury. Group 2 (n=6) consisted of animals that underwent grade IV liver injuries produced by a drill through a laparoscopic procedure and had closed cavity ClotFoam application. In this group, the agent was administered into the peritoneal cavity blindly without direct injury visualization or direction. Group 3 (n=4) consisted of animals that underwent grade 4 liver injuries through an open midline laparotomy without ClotFoam treatment (open controls). Group 4 (n=3) underwent grade 4 liver injuries through the laparoscopic technique without ClotFoam treatment (laparoscopic controls).

In all groups, 150 cc of ClotFoam was used for treatment. The ClotFoam was delivered via a mixing device into the abdominal cavity. Fluid resuscitation with Lactated Ringer's (LR) was begun immediately after injury. LR was infused as necessary to re-establish a MAP within at least 80% of the pre-injury MAP if possible.

Resuscitation was continued for the entire observation period. At the end of the 60 minute study, each animal's MAP and the total resuscitation volume infused were recorded.

After completion of the study period, the abdomen was examined. Liquid blood was suctioned. Blood clots were removed and weighed. In the gauze packing group, additional liquid blood loss was calculated by subtracting the wet gauze weight from dry gauze weight. Total blood loss was determined by adding liquid and clotted blood losses.

Figure 12:
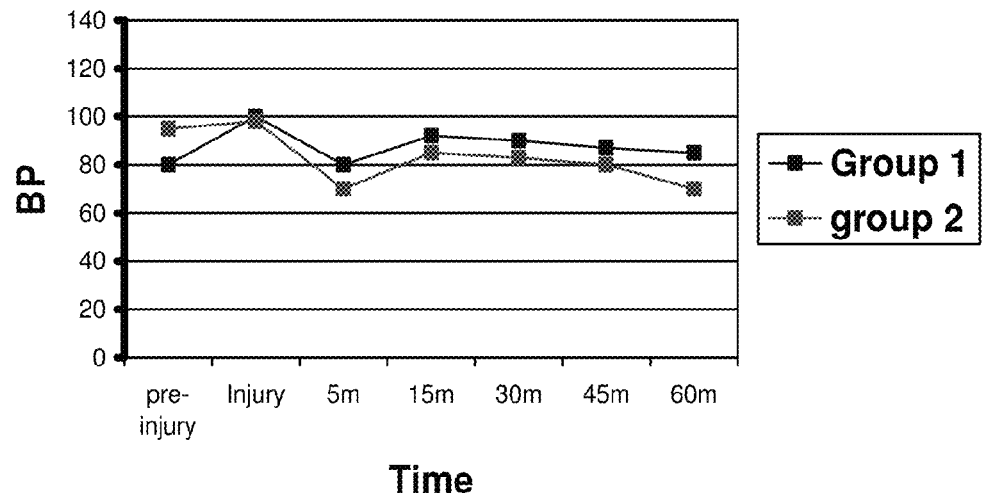
FIG. 12 Trend of mean arterial pressures (MAPs) in liver grade IV injury treated with ClotFoam (swine model)
FIG. 13 Trend of mean arterial pressures (MAPs) in liver grade IV injury, not-treated (swine model)

Animal survival was defined as the presence of a heart rate at the end of the study period. At 60 minutes, surviving animals were euthanized with 10 ml of Euthasol. Results: End points for animals in Groups 1 and 2 (Grade IV injuries) are shown in Table 6. Trend of mean arterial pressures (MAPs) are seen in FIG. 18 (treated). FIG. 12

TABLE 6

Outcome measures for Grade IV liver injuries treated with ClotFoam.

| Group | Survival Time (min) | Total Blood Loss (ml) | Fluid Requirement (ml) |
|---|---|---|---|
| 1 (n = 5) | 60 ± 0 | 300 ± 283 | 1500 ± 283 |
| 2 (n = 5) | 60 ± 0 | 600 ± 212 | 2175 ± 742 |

Group 1 = open cavity, Group 2 = closed cavity.
All values reported as mean ± SEM Controls:

Animals underwent grade IV liver injuries (3 laparoscopic and 4 open) to validate the laparoscopic model against the established open model. These animals were not treated with ClotFoam. Endpoints are seen in Table 7.

TABLE 7

Outcome measures for Grade IV liver injuries
without treatment (Controls).

| Group | Survival Time (min) | Total Blood Loss (ml) | Fluid Requirement (ml) |
|---|---|---|---|
| 3 (n = 4) | 26 ± 3 | 1900 ± 424 | 3050 ± 70 |
| 4 (n = 4) | 22 ± 11 | 1700 ± 200 | 2467 ± 569 |

Figure 13:
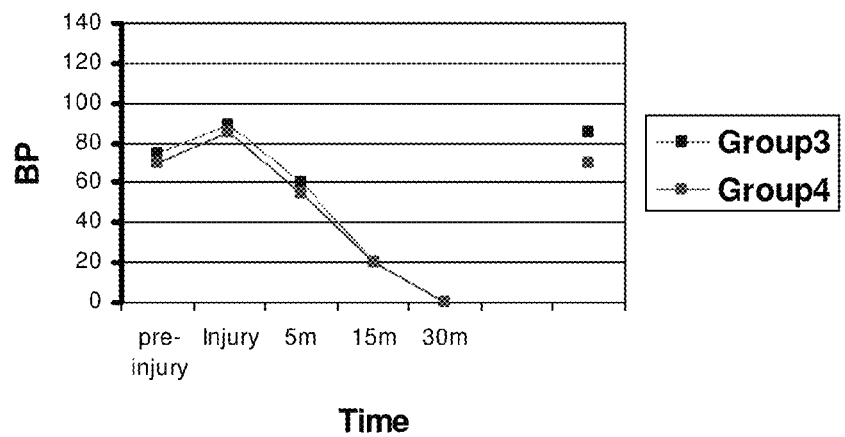

Group 3 = open laparotomy, Group 2 = laparoscopic.
All values reported as mean ± SEM Trend of MAPs for Grade 4 liver injuries of controls untreated with ClotFoam are shown in FIG. 13.

Clot Histology

Liver section samples were collected from all animals at necropsy. Samples of liver, containing the wounded site, were preserved in 5% formalin and processed using standard histology techniques. Fixed tissue samples were embedded in paraffin wax (melting point 56° C.) and sectioned at 2-3 μm. Glass-slide-mounted sections were then stained with hematoxylin and eosin (H&E). Two liver sections perpendicular to the resection site were evaluated per animal.

8. GLP Studies in the Swine

Effectiveness: We compared the effectiveness of ClotFoam hemostatic treatment without compression in Yorkshire crossbred swine, age 2.5 months, weighing 37±2 kg. We tested Clot foam in three surgical protocols: Hepatectomy, Partial via open midline laparotomy and Spleen Laceration,—assigning 20 animals to the protocol. The protocols were approved by the Institutional Animal Care and Use Committee. Animals were randomized into 2 groups. Group 1 (n=14) consisted of animals that received ClotFoam application following injury. Group 2 (n=6) consisted of animals that received GELFOAM (Pfizer) following injury versus GelFoam (Pfizer) to stop moderate to severe bleeding. The studies were designed to determine whether the hemostatic can control intraoperative hemorrhage within 10 minutes of application.

Surgical Procedures:

We tested Clot foam in three surgical protocols: Hepatectomy, Partial nephrectomy and Spleen laceration via open midline laparotomy, assigning 20 animals to each protocol, or a total of 60 animals. The protocols were approved by the Institutional Animal Care and Use Committee. Animals were randomized into two arms.

Group 1 (n=14) consisted of animals that received ClotFoam application following injury.

Group 2 (n=6) consisted of animals that received GELFOAM (Pfizer) following injury to stop moderate to severe bleeding. Animal numbers were determined by using a power analysis set to the standard of 0.8. The studies were designed to determine whether the hemostatics can control intraoperative hemorrhage without compression within 5 minutes of application. Ability to achieve hemostasis within 5 minutes of application without compression and with no re-bleeding within 10 minutes demonstrated the therapeutic benefit of the hemostatic sealant. Once the hemostasis was assessed, the abdominal incision was closed. Animals that did not reach hemostasis within 10 minutes were euthanized. Upon termination of experiments at 14 or 15 days, surviving animals were euthanized, surgical areas inspected, and tissue recovered for macroscopic and microscopic examinations.

Hepatectomy Model:

A partial right hepatectomy was performed in which the distal 4 cm right lobe of the liver was sharply divided and removed. Bleeding was permitted for 10 seconds. 40CC of ClotFoam was applied, and hemostasis was assessed at 5 minutes. Partial nephrectomy: The kidney was completely immobilized from the retroperitoneum. The distal 3 cm of the apex of the kidney was sharply divided and removed, and permitted to bleed for 10 seconds. ClotFoam will be applied and hemostasis was assessed at 5 minutes.

Spleen Laceration:

A 3×3 cm square laceration was created and removed from the anterior surface of the spleen and permitted to bleed for 10 seconds. ClotFoam was applied, and hemostasis was evaluated at 5 minutes.

Results: Number of animals that reached hemostasis per procedure

| Group | N | Procedure | Number of animals reaching Hemostasis within 5 minutes | Termination at day 15 | Necropsy | Histology | IgE |
|---|---|---|---|---|---|---|---|
| 1(GF) | 6 | Hepatectomy | None | None | None | None | 6 (control) |
| 2(CF) | 14 | Hepatectomy | 14 | 14 | 14 | 14 | 14 |
| 3(GF) | 6 | Nephrectomy | None | none | None | None | None |
| 4(CF) | 14 | Nephrectomy | 12 | 11 | No | 11 | 11 |
| 5(GF) | 6 | Spleen | 13 | 8 | 8 | 8 | 8 |
| 6(GF) | 14 | Spleen | None | None | None | None | None |

Acronyms: GF = GelFoam; CF = ClotFoam

Immune Response:

There were no significant differences in OD readings observed with sera collected on day 0, day 7 or day 14 from control and ClotFoam treated pigs when tested against gelatin or BSA. We conclude that experimental pigs produced no detectable antibodies against gelatin or BSA at the times tested.

Biocompatibility and Biodegradation (Histology)

Most organs have normal appearance. ClotFoam-treated animals as compared from to samples taken from a sham specimen. Abnormalities were noted in lungs of all animals (lymphocytic infiltration). Inflammatory changes and lymphocytic infiltration was were seen in gut tissues and in the abdominal wall. The inflammatory changes appear due to the internal trauma and to a normal inflammatory reaction to a foreign body (ClotFoam).

CONCLUSION

The data from this study indicates that ClotFoam was 100% successful in achieving intraoperative hemostasis for a liver wound that produced severe hemorrhage. Since hemostasis was achieved within 5 minutes, we conclude that the use of ClotFoam requires shorter time to achieve hemostasis than conventional suturing methods utilized in laparoscopic procedures.

What is claimed is:

1. A hemostatic composition containing 4 solutions comprising the ingredients described in portions a)-d), for cessation of blood loss from injured tissue of a patient's body without application of a compressive force:
   a) Teleostean (fish) gelatin type A mixed with sucrose, polyvinylpyrrolidone, a water-soluble foam inducer of sodium bicarbonate and dihydrogen phosphate, and human serum albumin in a buffer solution at a pH of about 8.3 in the presence of metallic ions and a gel enhancer selected from the group consisting of alpha-galactosidase degraded carrageenan, alginate sulfate, hyaluronic salt, or hyaluronic acid;
   B) polyacrylic acid crosslinked with allyl ethers of sucrose (Carbomer homopolymer) containing not less than 56.0 percent and not more than 68.0 percent of carboxylic acid; with a viscosity of a neutralized 0.5 percent aqueous dispersion between 30,500 and 39,400 centipoises;

c) fibrin monomer in a acidic solution pH 3.4 to pH4.0 that polymerizes upon change in pH from acid to neutral (7.0-7.2); and d) calcium independent transglutaminase enzyme and calcium chloride in HEPES buffer for stabilizing the fibrin polymer.

2. A composition as claimed in claim 1 wherein said alkaline buffer solution of said a) has a concentration in the range of about 0.5M and 0.75M sodium carbonate/bicarbonate.

3. A composition as claimed in claim 1, wherein said d) comprises a source of calcium ions in a concentration of about 20 mM suitable for polymerization of the fibrin monomer.

4. A composition as claimed in claim 1, wherein said divalent ions of said b) are selected from the group comprising calcium, zinc and magnesium ions, wherein said divalent ions substantially increase the rate of fibrin polymerization, the length and strength of fibrin filaments, and reduces the time needed for scaffold polymerization.

5. A composition as claimed in claim 1, wherein said composition can be rendered sterile by a combination of autoclaving UV radiation, and filtration methods.

6. A composition as claimed in claim 1, wherein said fibrin monomer concentration of said c) is within the range of about 12 mg/ml and 40 mg/ml of fibrin in acetic.

7. A composition as claimed in claim 1, wherein said composition is non-inflammatory and bio-compatible with tissue on which it is applied.

8. A composition as claimed in claim 1, wherein the cessation of blood loss refers to refers to controlling blood loss following intraoperative hemorrhage or trauma.

9. A composition of four solutions as claimed in claim 1, wherein, the addition of the gel enhancer in solution a, upon mixture of the 4 solutions produce a 3-D polymer with vicoelastic properties defined by strength measured as rheometric value g' superior to 6,000 dyn/cm$^2$ which allows the composition to resist the flow of blood, and remain in place over the wound.

10. A composition as claimed in claim 1, wherein said gel enhancer of

11. A composition as claimed in claim 1, wherein said fibrin monomer of said solution c) is substantially free of thrombin and exogenous enzymes that catalyze the premature polymerization of fibrin monomer during storage.

12. A method of sealing injured tissue of a patient's body that utilizes a hydrogel carrier and a fibrin monomer, in combination, for cessation of blood loss from the injured tissue without application of a compressive force independently therefrom, the method comprising the steps of:

a) mixing in a mixing device the following components to create a foam: an hemostatic composition a first component (a), of Teleostean (fish) gelatin type A mixed with sucrose, polyvinylpyrrolidone, a water-soluble foam inducer of sodium bicarbonate and dihydrogen phosphate, human serum albumin and a gel enhancer selected from the group consisting of alpha-galactosidase degraded carrageenan, alginate sulfate, hyaluronic salt, or hyaluronic acid. in a buffer solution at a pH of about 8.3 in the presence of metallic ions;

(ii) a second component (b) of polyacrylic acid cross-linked with allyl of sucrose (Carbomer homopolymer) containing not less than 56.0 percent and not more than 68.0 percent of carboxylic acid; with a viscosity of a neutralized 0.5 percent aqueous dispersion between 30,500 and 39,400 centipoises.

(iii) a third component (c) of a fibrin monomer in acidic solution pH 3.4 to pH 4.0 that polymerizes upon change in pH from acid to neutral (7.0-7.2); and (iv) a fourth component (d) of calcium independent transglutaminase enzyme and calcium chloride in HEPES buffer for stabilizing/crosslinking the fibrin polymer;

(b) delivering and/or dispersing the foam through an outlet of the mixing device to a surgical site of a body cavity, organ or tissue so as to place the foam in contact with the site such that the non-dynamic, non-crosslinked fibrin monomer of the foam sticks to wet tissue of the site and forms a matrix in the patient's blood; and wherein the mixing of solutions a, b, c and d renders the non-crosslinked fibrin monomer dynamic by neutralizing its pH of the overall mixture such that the non-crosslinked fibrin is converted to a fibrin sealant, thereby inducing coagulation of the blood and adhesive properties of severed tissue.

13. The method set forth in claim 12, wherein the surgical site includes at least one of the patient's skin, abdominal cavity, thorax, cardiovascular system, lymphatic system, pulmonary system, ear(s), nose, throat, eye(s), liver, spleen, cranial, spinal, maxillo-facial, bone, tendon, pancreas, genitourinary tract or alimentary tract.

14. The method set forth in claim 12, wherein the mixing device is a pneumatically operated, four-barreled syringe, each barrel containing one of component and solutions a, b, c and d.

15. The method set forth in claim 12, wherein the adhesive foaming hydrogel is formed in less than about 10 seconds of mixing component solutions a c, b, and d.

16. The method set forth in claim 12, wherein the adhesive foaming hydrogel formed attains a storage moduli (G') of about 6000 dyn/cm2 monitored by rheometry as a function of time at a frequency of around 5 Hz and a about 2% stress strain at approximately 37° C.

17. The method set forth in claim 12, wherein foam formation is induced by a chemical reaction between the polyacrylic acid and sodium monobasic phosphate ($NaH_2$—$PO_4$) in mixture with a simple buffer solution of sodium bicarbonate ($NaHCO_3$) such that carbon dioxide ($CO_2$) is released in the presence of divalent ions or surfactants.

18. The method set forth in claim 12, wherein the foam produced upon mixing of component Parts A, B, C and D is a non-exothermic foam having a volume about 400% greater than that of the component Parts before mixing step (ai).

19. A method as claimed in claim 12, wherein said gel enhancer of said a) is non-inflammatory.

20. A composition as claimed in claim 1, wherein the fibrin monomer can be dissolved either in acetic acid or an acidic buffer.

21. A composition as claimed in claim 1, wherein the addition of a gel enhancer made of hyaluronic acid prevents or reduces the formation of adhesions following intracavitary surgery.

* * * * *